US009789268B2

(12) United States Patent
Hart et al.

(10) Patent No.: US 9,789,268 B2
(45) Date of Patent: Oct. 17, 2017

(54) TRANSVAGINAL SPECIMEN EXTRACTION DEVICE

(71) Applicants: Stuart Richard Hart, Tampa, FL (US); Philip James Hipol, Tampa, FL (US); Mario Alves Simoes, Pinellas Park, FL (US); Mark Antoine Zakaria, Tampa, FL (US)

(72) Inventors: Stuart Richard Hart, Tampa, FL (US); Philip James Hipol, Tampa, FL (US); Mario Alves Simoes, Pinellas Park, FL (US); Mark Antoine Zakaria, Tampa, FL (US)

(73) Assignee: University of South Florida, Tampa, FL (US)

( * ) Notice: Subject to any disclaimer, the term of this patent is extended or adjusted under 35 U.S.C. 154(b) by 37 days.

(21) Appl. No.: 14/297,166

(22) Filed: Jun. 5, 2014

(65) Prior Publication Data

US 2014/0288486 A1    Sep. 25, 2014

Related U.S. Application Data

(63) Continuation of application No. PCT/US2012/070147, filed on Dec. 17, 2012.
(Continued)

(51) Int. Cl.
*A61M 13/00* (2006.01)
*A61M 25/00* (2006.01)
(Continued)

(52) U.S. Cl.
CPC .......... *A61M 13/003* (2013.01); *A61B 10/04* (2013.01); *A61B 17/42* (2013.01); *A61M 25/007* (2013.01);
(Continued)

(58) Field of Classification Search
CPC .. A61M 25/007; A61M 13/00; A61M 13/003; A61M 25/0082;
(Continued)

(56) References Cited

U.S. PATENT DOCUMENTS 5,520,698 A    5/1996   Koh
5,545,161 A *  8/1996   Imran ................ A61B 18/1492
                                                        606/41
(Continued)

FOREIGN PATENT DOCUMENTS

WO    WO9745053    12/1997

OTHER PUBLICATIONS

Dapri, Giovanni. Single Access Laparoscopic Surgery: Complementary or Alternative to NOTES? World Journal of Gastrointestinal Surgery 2010. Jun. 27; 2(6): 207-209.
(Continued)

*Primary Examiner* — Kevin C Sirmons
*Assistant Examiner* — Shefali Patel
(74) *Attorney, Agent, or Firm* — Robert J. Varkonyi; Smith & Hopen, P.A.

(57) ABSTRACT

In laparoscopic surgery, small (5-12 mm diameter) incisions are made in an abdominal wall through which instruments dissect and remove specimens that may be several centimeters in diameter. Removal of a sample typically requires either enlarging these incisions or morcellating the sample to pass through sub-centimeter ports. A laparoscopic device permits extraction of the sample to be removed in a female using a vagina, which has sufficient elasticity to accommodate removal of large specimens. A posterior portion of the vagina communicates to an abdomen through a few tissue layers, and is distant from vital anatomic structures. Utilizing the vagina is optimal due to its ease of access to the abdomen and repair, minimal scarring and post-operative
(Continued)

pain, and faster recovery following surgery. A deployable collection bag is housed in a sheath, which is deployed into the vagina or an abdominal cavity to extract a large (multiple-centimeter) specimen(s) through the vagina. An optional insufflation system and an inflatable balloon to maintain a pneumoperiotoneum may be used to reduce a number of laparoscopic ports required.

17 Claims, 14 Drawing Sheets

Related U.S. Application Data

(60) Provisional application No. 61/576,759, filed on Dec. 16, 2011.

(51) Int. Cl.
    *A61B 10/04* (2006.01)
    *A61B 17/42* (2006.01)
    *A61B 17/00* (2006.01)
    *A61B 17/34* (2006.01)

(52) U.S. Cl.
    CPC ............. *A61M 25/0082* (2013.01); *A61B 2017/00287* (2013.01); *A61B 2017/00424* (2013.01); *A61B 2017/345* (2013.01); *A61M 2025/0096* (2013.01); *A61M 2210/1475* (2013.01)

(58) Field of Classification Search
    CPC .. A61M 2025/0096; A61M 2210/1475; A61B 10/04; A61B 17/42
    See application file for complete search history.

(56) References Cited

U.S. PATENT DOCUMENTS

| | | | |
|---|---|---|---|
| 5,643,285 | A | 7/1997 | Rowden et al. |
| 6,544,248 | B1 * | 4/2003 | Bass .................. 604/511 |
| 6,572,631 | B1 | 6/2003 | McCartney |
| 7,399,290 | B2 * | 7/2008 | Maki ................ A61M 1/0058 604/96.01 |
| 7,806,888 | B2 * | 10/2010 | Frassica ..................... 604/523 |
| 8,082,925 | B2 | 12/2011 | McCartney |
| 2004/0138587 | A1 | 7/2004 | Lyons, IV |
| 2010/0305566 | A1 | 12/2010 | Rosenblatt et al. |
| 2011/0092982 | A1 | 4/2011 | Hahn et al. |
| 2011/0190782 | A1 | 8/2011 | Fleming et al. |

OTHER PUBLICATIONS

Ghezzi, F. Vaginal Extraction of Pelvic Masses Following Operative Laparoscopy. Surgical Endoscopy 2002. vol. 16. pp. 1691-1696.

Castro-Perez, R. Minilaparoscopic-assisted Transvaginal Approach in Benign Liver Lesions. Rev Esp Enferm Dig, 2010. vol. 102, No. 6, pp. 357-364.

Spuhler, S. Extracteur Vaginal CCL Pour Coeliochirurgie. Archives of Gynecology and Obstetrics, 1993, 253 [Suppl]: S80-S82.

Sphuler, S. A New Vaginal Extractor for Laparoscopic Surgery. The Journal of the American Association of Gynecologic Laparoscopists, 1994; 1 (4 Pt 1): 401-4.

International Search Report and Written Opinion issued by the International Searching Authority on Apr. 22, 2013 for international patent application No. PCT/US2012/070147.

Karl Storz Endoskope. Hybrid Procedures. http://www.karlstorz.com/cps/rde/xchg/SID-6C9ED754-D894A4EA/karlstorz-en/hs.xsl/8874.htm [Dec. 13, 2012 10:55:50 AM].

Karl Storz Endoskope. ROTOCUT G1 Morcellator. http://www.karlstorz.com/cps/rde/xchg/SID-6C9ED754-D894A4EA/karlstorz-en/hs.xs1/1397.htm [Dec. 13, 2012 10:59:24 AM].

Karl Storz Endoskope. Transvaginal Hybrid Procedures. Notes 21. Jun. 2012-E.

International Preliminary Report on Patentability issued by the International Bureau on Jun. 26, 2014 for international patent application No. PCT/US2012/070147.

Extended Search Report issued by the European Patent Office on Mar. 18, 2015 for European Patent Application No. 12857385.4-1654.

Partridge, A.J. Medical Memoranda. The Third Case of Fatal Air Embolism Reported after Vaginal Insufflation. British Medical Journal. Sep. 11, 1943. p. 329.

\* cited by examiner

TRANSVAGINAL SPECIMEN EXTRACTION DEVICE

CROSS-REFERENCE TO RELATED APPLICATIONS

This application is a continuation of and claims priority to International Patent Application No. PCT/US2012/070147, filed on Dec. 17, 2012 which claims priority to U.S. Provisional Patent Application No. 61/576,759, entitled, "Transvaginal Specimen Extraction Device," filed on Dec. 16, 2011, the contents of which are herein incorporated by reference.

FIELD OF THE INVENTION

This invention relates to laparoscopic instrumentation and use. Specifically, the invention discloses an endoscopic instrument for transvaginal surgery.

BACKGROUND OF THE INVENTION

Laparoscopic surgical techniques have been developed in order to avoid large skin incisions associated with traditional surgery, using small incisions (of 5-12 mm) in which surgical instruments are inserted. These surgical instruments may be used to dissect and remove tissues and organs (specimens) which may be several centimeters in diameter. Such minimally invasive surgical techniques have been evolving for more than 100 years, since Georg Kelling performed the first experimental laparoscopy in 1901. (Litynski, G. Endoscopic surgery, the history, the pioneers. World J. Surg. 1999 August; 23(8):745-53). These minimally invasive laparoscopic surgeries result in less postoperative pain, quicker recovery and an improved cosmetic appearance for patients compared to traditional laparotomy. Currently, hybrid procedures combining flexible endoscopy and laparoscopy, such as intraoperative enteroscopy and laparoscopic-assisted endoscopic retrograde cholangiopancreatography, are performed in increasing numbers. (Ceppa, F., et al. Laparoscopic transgastric endoscopic retrograde endoscopy after Roux-en-Y gastric bypass. Surg. Obes. Relat. Dis. 3: 21-24 2007; Peters, M., et al. Laparoscopic transgastric endoscopic retrograde cholangiopancreatography for benign common bile duct structure after Roux-en-Y gastric bypass. Surg. Endosc. 16:1106 2002).

One limitation, however, has been the removal of pathologic specimens that are larger than the port sites used to perform these surgeries. In abdominal laparoscopy, it is impossible to remove large specimens without cutting or morcellating the specimen within the abdominal cavity or making an incision in the abdominal wall that is large enough to accommodate removal of the large specimen. Recently, surgeons have taken advantage of natural orifices (vagina, rectum, urethra, and gastrointestinal tract) to perform Natural Orifice Transluminal Endoscopic Surgery (NOTES) procedures with good results (Bessler, M.; Gumbs, A. A.; Milone, L.; Evanko, J. C.; Stevens, P.; Fowler, D. Video. Pure natural orifice transluminal endoscopic surgery (NOTES) cholecystectomy. Surg Endosc 24: 2316-2317; 2010; Kaouk, J. H.; White, W. M.; Goel, R. K.; Brethauer, S.; Crouzet, S.; Rackley, R. R.; Moore, C.; Ingber, M. S.; Haber, G. P. NOTES transvaginal nephrectomy: first human experience. Urology 74: 5-8; 2009). NOTES has been used for diagnostic and therapeutic procedures including) organ removal, though current articulating instruments for use with NOTES are disposable, increasing costs compared to standard laparoscopic procedures, and removal of large tumors or solid organs cannot be performed using NOTES (Dapri, Single access laparoscopic surgery: Complementary or alternative to NOTES? World J Gastrointest Surg. 2010 Jun. 27; 2(6): 207-9). Advantages of NOTES include cosmetic results, reduced anesthesia requirements; faster recovery and shorter hospital stays; decreased abdominal trauma and therefore potential complications of transabdominal wound infections, such as hernias, less need for immunosuppression and pain killers; and better postoperative pulmonary and diaphragmantic function.

Another limitation in traditional laparoscopic surgery is the size of the instruments used. A typical umbilicus laparoscopic port incision is no larger than 15 mm, and other support incisions are usually much smaller. Larger incisions lead to more scarring and the potential for hernia formation. Therefore, the tools used for laparoscopy are small in size to fit these incision limitations.

The vagina is the ideal portal to access the abdominal cavity for women undergoing minimally invasive laparoscopic surgery, and is regaining interest in the surgical community (Auyang, E. D.; Santos, B. F.; Enter, D. H.; Hungness, E. S.; Soper, N. J. Natural orifice translumenal endoscopic surgery (NOTES((R))): a technical review. Surg Endosc 25: 3135-3148; 2011; Stark, M.; Benhidjeb, T. Natural Orifice Surgery: Transdouglas surgery—a new concept. JSLS 12: 295-298; 2008) for peritoneal access. According to some computer generated models (Ashton-Miller, J. A.; DeLancey, J. O. Functional anatomy of the female pelvic floor. Ann N Y Acad Sci 1101: 266-296; 2007), its elasticity allows stretching to accommodate dimensions greater than three times its resting state. Accordingly, transvaginal NOTES is considered one of the safest and feasible methods for clinical application. Transvaginal cholecystectomy has been experimentally performed without using laparoscopic assistance.

Ghezzi et al. (Ghezzi, F.; Raio, L.; Mueller, M. D.; Gyr, T.; Buttarelli, M.; Franchi, M. Vaginal extraction of pelvic masses following operative laparoscopy. Surg Endosc 16: 1691-1696; 2002.) and Spuhler et al. (Spuhler, S. C.; Sauthier, P. G.; Chardonnens, E. G.; De Grandi, P. A new vaginal extractor for laparoscopic surgery. J Am Assoc Gynecol Laparosc 1: 401-404; 1994) described devices for the extraction of pelvic masses following laparoscopy. These devices utilized a metal shaft with a fitted rubber ball to provide vaginal occlusion and prevent loss of pneumoperiotoneum. Another device developed in Australia and marketed by Gynetech Pty Ltd, uses a similar hollow tube placed in the vagina (McCartney, A. J. Transvaginal tube as an aid to laparoscopic surgery. Google Patents; 2003). The design of this device is such that the tube fits around the cervix to distinguish the cervicovaginal junction, similar to the Koh colpotomy cup already in use for hysterectomy procedures (Koh, C. H. Simplified total laparoscopic hysterectomy method employing colpotomy incisions. Google Patents; 1996).

However, to date, there are no devices marketed in the U.S. aimed at utilizing the vagina as an access to the peritoneal cavity for the introduction of laparoscopic surgical devices or implants, or the extraction of pathologic specimens. Accordingly, there is a need in the art for devices that permit enhanced access to the abdomen during surgery.

SUMMARY OF THE INVENTION

Recently, natural orifice transluminal endoscopic surgery (NOTES) has been performed by entering the peritoneal cavity via the stomach, colon, vagina, or bladder. (Pearl, J., Ponsky, J., Natural orifice transluminal endoscopic surgery: past present and future. J Min. Acc. Surg. 3:2 43-46 2008; Wilk, P., U.S. Pat. No. 5,297,536). NOTES has been extensively studied in animal models, with tubal ligation, gallbladder surgery, oophorectomy, hysterectomy, gastrojejunostomy, and splenectomy having been described. (Jagannath, S., et al. Peroral transgastric endoscopic ligation of fallopian tubes with long-term survival in a porcine model. Gastrointest. Endosc. 61: 449-453 2005; Experimental studies of transgastric gallbladder surgery: cholecystectomy and cholecystogastric anastomosis. Gastrointest. Endosc. 61: 601-606 2005; Wagh, M. et al., Survival studies after endoscopic transgastric oophorectomy and tubectomy in a porcine model. Gastrointest. Endosc. 63: 473-478 2008; Merrifield, B., et al. Peroral transgastric organ resection: a feasibility study in pigs. Gastrointest. Endosc. 63: 693-697 2006; Kantsevoy, S., et al. Transgastric endoscopic splenectomy: is it possible? Surg. Endosc. 20: 522-525 2006). These surgical procedures are promising advances, due to the potential to eliminate traditional surgical complications, like postoperative abdominal wall pain, wound infections, hernias, adhesions, and impaired immune function. (Wagh, M., Thompson, C. Surgery insight: natural oriice transluminal endoscopic surgery—an analysis of work to date. Gastr. & Hept. 4:7 386-392 2007). Further, NOTES procedures may be performed under conscious sedation and not general anesthesia. (Pearl, J., Ponsky, J., Natural orifice transluminal endoscopic surgery: past present and future. J Min. Acc. Surg. 3:2 43-46 2008). The transluminal approach could be particularly important for morbidly obese patients and others at high risk for standard surgery.

The vagina is the ideal portal to access the abdominal cavity for women undergoing minimally invasive laparoscopic surgery. According to some computer generated models (Ashton-Miller, J. A.; DeLancey, J. O. Functional anatomy of the female pelvic floor. Ann N Y Acad Sci 1101: 266-296; 2007), its elasticity allows stretching to accommodate dimensions greater than three times its resting state. The posterior portion of the vagina also directly communicates with the abdomen through only a few tissue layers, and when placed on stretch, is distant from vital anatomic structures. A laparoscopic port utilizing transvaginal access would increase the surgeon's access to the abdominal cavity and provide a much larger incision site, without the concerns for hernia formation and scarring. Additionally, transvaginal removal of large specimens enables minimally invasive laparoscopic surgery without the need for morcellation within the abdominal cavity or large incisions in the abdominal wall to remove the specimens, thereby minimizing scarring and allowing faster recovery following surgery.

As such, the present invention provides an instrument adapted to provide access to the abdomen through the vagina. The instrument allows for the introduction of devices and implants, as well as the removal of tissues or organs (i.e., "specimens") from a woman's abdominal cavity during minimally invasive surgery. The instrument comprises a tubular shaft having a proximal end and a distal end made from any material known useful in the art for trocars or surgical instruments, such as plastic, resin, or metal. Exemplary metals include steel, like surgical steel, surgical steel, titanium, and aluminum. Useful plastics and resins include polyurethane, polyvinyl chloride, polytetrafluoroethylene, polyester, para-phenylenediamine and terephthaloyl chloride polymer, meta-phenylenediamine and terephthaloyl chloride polymer, nylon, rubber, latex, silicone, polyisoprene, polystyrene and polybutadiene polymer, urethane, polyethylene, polyisoprene, ethylene propylene diene monomer, neoprene, polyurethane, polyvinyl chloride, thermoplastic, and styrene butadiene. polyethylene terephthalate, polypropylene, polycarbonate polyetherimide, acrylonitrile butadiene styrene, vinyl ester, polyurethane, cyanate ester, polycyanurate, polystyrene plastic, acrylic, thermoplastic composite, polyester composite, epoxy resin composite, or melamine resin composite. Composite materials may include any fiber known in the art that is useful for forming solid or semi-solid structures, such as carbon fiber and aramids like Kevlar, Twaron, Nomex, New Star and Teijinconex. The tubular shaft may be straight or curved, and optionally includes a hemispherical end disposed on the distal end of the shaft. The tubular shaft may be additionally designed to conform more exactly to the shape of the vagina. The tubular shaft has at least an access opening disposed on the tubular shaft wall on the distal end of the shaft. Optionally, the tubular shaft may have an actuator mechanism disposed along the length of the shaft or a portion thereof to aid in deployment of a specimen bag. Optionally, elevations or raised features are disposed distally and proximally to the access opening to provide visual and haptic target for placement of an incision. A handle is optionally disposed on the proximal end of the shaft.

Optionally, a deployable specimen collector is disposed within the tubular shaft; adjacent to the access opening. The specimen collector is formed of a specimen bag, a deployable ring, and a specimen bag support. The specimen bag is made of any durable, flexible material known in the art, such as silk, nylon, polyester, and acrylic, and is designed with an open end and a closed end. The deployable ring is disposed on the open end of the specimen bag, and is made of any semi-flexible material known in the art, such as thin wire, thin flexible plastic, and other materials that may bend. This permits the specimen bag to convert from collapsed, within the tubular shaft, to being able to accept a specimen. A specimen bag support is in communication with the deployable ring, and connected to an actuator mechanism. The specimen bag support may be any means, such as a connector bar, which may be made of any materials known in the art such as surgical steel, plastic, and titanium, and permits the actuator mechanism to advance the deployable ring by the surgeon.

The laparoscopic instrument optionally includes a means to insufflate the abdomen of the patient. An insufflation port is disposed on the proximal end of the laparoscopic instrument, such as on the tubular shaft or on the handle, where one is provided. The insufflation port is in fluid communication with the interstitial space of the tubular shaft, or to an insufflation channel disposed in the interstitial space of the tubular shaft. The insufflation channel ends in the distal third of the tubular shaft, such as forming a port on the distal end of the tubular shaft.

The laparoscopic instrument is optionally circumscribed by an inflatable balloon disposed on an exterior face of the tubular shaft. The inflatable balloon is in fluid communication with an inflation source, such as through an inflation channel. The inflation channel may be disposed on an exterior face of the tubular shaft or disposed on an interior face of the tubular shaft. Optionally, the proximal end of the inflation channel is in fluid communication with an inflation port. Variations of the instrument include surgical instrument seals, which may be made of one or more flexible compounds such as polyester, para-phenylenediamine and terephthaloyl chloride polymer, carbon fiber, expanded PTFE, meta-phenylenediamine and terephthaloyl chloride polymer, nylon, fiber glass, cotton, polypropylene and ceramic, rubber, latex, silicone, polyurethane, polyisoprene, polystyrene and polybutadiene polymer, urethane, polyethylene, polyisoprene, polyvinylchloride, ethylene propylene diene monomer, neoprene, and styrene butadiene. The seals may also be is coated a lubricant. Exemplary lubricants include hydrophilic polymer coatings, Teflon, cyanoacrylate, parylene, plasma surface treatments, cornstarch powder, silicone oil, silicone grease, astroglide lubricants, mineral oil, glycerin, alcohol, saline, Teflon lubricants, Krytox lubricants, molybdenum disulfide lubricants, and graphite. However, other lubricants known in the art may be used.

The posterior cul-de-sac, also known as the Pouch of Douglas, illustrated in FIG. 8, has traditionally been considered a safe access site to enter the abdominal cavity through a vaginal incision. Alternatively, access to the Pouch of Douglas can be made laparoscopically, and posterior to the cervix in a patient. The laparoscopic instrument of the invention can be safely placed through a posterior vaginal incision into the abdomen with either technique, and the laparoscopic instrument is useful in performing removal of a specimen from a patient by providing a laparoscopic instrument as described above. The laparoscopic instrument is introduced into a patient's vagina and positioned adjacent to a structure in the vagina, such as the Pouch of Douglas. Optionally an incision is made. The specimen bag is extended through the specimen bag opening and the specimen placed in the specimen bag. The specimen bag is then retracted and the laparoscopic instrument withdrawn from the patient's vagina. Optionally, the patient's abdomen may be insufflated using variations of the device, by providing an insufflation system in the laparoscopic instrument. A closed insufflation system may be used, having an insufflation port attached to the proximal half of the laparoscopic instrument, an insufflation channel in fluid communication with the insufflation port, and a port disposed on the distal end of the laparoscopic instrument, in fluid communication with the insufflation channel. Alternatively, an open insufflation system may be used, having an insufflation port disposed on the proximal half of the laparoscopic instrument, where the insufflation port is in fluid communication with the interstitial space of the tubular shaft. A fluid, such as is air or $CO_2$, is introduced into the insufflation system, wherein the fluid insufflates the patient. To maintain insufflation, variations of the inventive laparoscopic instrument may be used having an inflatable balloon on the laparoscopic instrument, wherein the inflatable balloon is disposed on an exterior face of the tubular shaft and wherein the inflatable balloon is in fluid communication with an inflation source. A fluid, such as is air or $CO_2$, is introduced into the inflatable balloon, wherein the fluid inflates the inflatable balloon, thereby closing off the vaginal opening to maintain insufflation.

By using the natural elasticity characteristic of the vagina, surgeons can introduce large devices or implants, or extract large, multiple-centimeter specimens that are otherwise challenging to introduce or remove through traditional laparoscopic ports. The described laparoscopic instrument provides a novel approach to access the abdominal cavity and provide effective specimen removal through the vagina.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
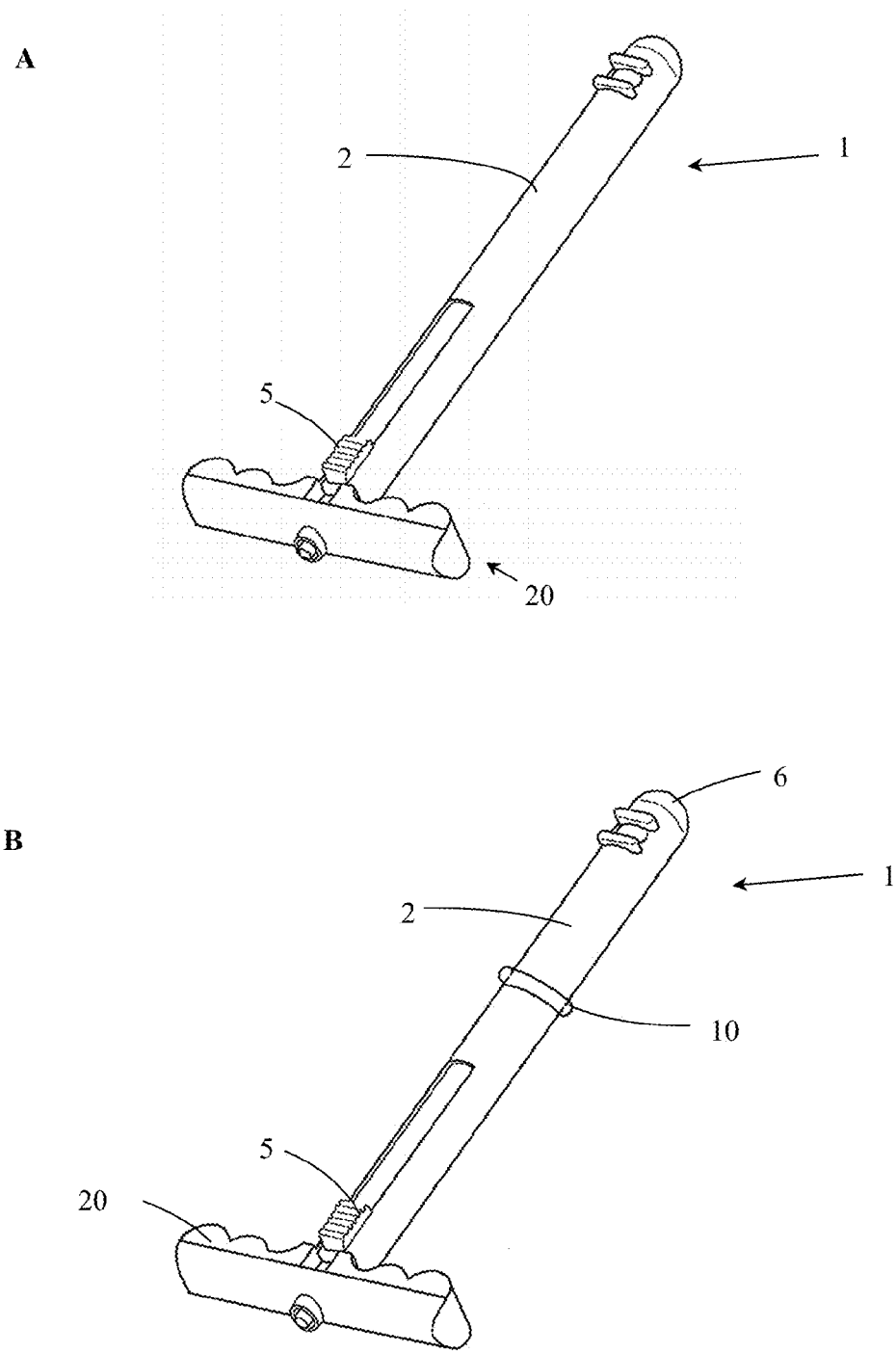
FIGS. 1(A) and (B) are isometric views of the present laparoscopic instrument (A) without an occlusion balloon; and (B) with the occlusion balloon deflated.

The vagina is an underutilized portal for use during laparoscopic surgery. This may be due, in part, to the paucity of medical devices and instruments designed for this mode of access. While there are some vaginal colpotomizer rings and uterine manipulators commercially available, there are no devices specifically designed for use in the vagina during laparoscopic surgery. This invention involves a device used during laparoscopic surgery that is used to extract tissues or organs, referred herein as "specimens", from a woman's abdominal cavity through the woman's vagina, or to introduce devices or implants into the abdomen during surgery. The device shaft was designed to accommodate the average dimensions of the animal's vagina, such as a human, with both a straight and curved design to allow the surgeon optimal flexibility when manipulating the device during actual use in laparoscopic surgical procedures. The inventive laparoscopic device uses a novel sheath and access opening. The sheath may also include a mechanism to deploy a pouch into a woman's abdominal cavity and extract large (multiple-centimeter) specimens through the vagina using traditional laparoscopic surgical technique. For added safety, the curved design also enables the surgeon to elevate the posterior aspect of the vagina further away from the rectosigmoid during surgical procedures. The handle grip was ergonomically designed to allow for ease of manipulation, deployment, and removal of the extraction bag through control of the actuator mechanism. With multiple applications including the retrieval of large abdominal masses and transfer of surgical instruments into the abdominal cavity, the laparoscopic device has the potential to expand the use of the vaginal opening as a natural surgical orifice while preserving the use of small port sites during the laparoscopic surgery. Unlike previously developed devices, it incorporates a actuator mechanism to deploy a specimen bag directly into the abdominal cavity. This device allows for removal of larger specimens than is possible through the abdomen, without the need for morcellation of tissue or enlarging incisions in the abdominal wall to remove them.

As used herein, "about" means approximately or nearly and in the context of a numerical value or range set forth means±15% of the numerical.

As used herein, the term "channel" refers to a path that directs fluid flow in a particular direction. The channel can be formed as a fully enclosed tube or conduit. The channel can have any cross-section known in the art, such as circular, square, rectangular, triangular, enclosed U-shaped, hexagonal, octagonal, irregular. The channel can have any configuration including, but not limited to, linear or curved, and may include different diameter sizes, such as due to different tubing being joined together.

As used herein, the term "curved" means the invention, when viewed from at least one angle, has a generally crescent shape, with one edge having a concave shape and the opposite edge having a convex shape. The angulation of the curve, i.e. curvature, may vary, for example having a customized curvature.

As used herein, the term "endoscope" or "scope" is used to refer to an endoscope, laparoscope, sigmoidoscope, proctoscope, colonoscope, or other types of medical endoscopes. As known to those skilled in the art, a typical endoscope generally comprises a connecting tube, a handle and an insertion tube (the part inserted into the patient).

As used herein, the term "hemispherical" means a configuration that is a portion of a sphere, including a half sphere, though does not require a full 180° arc and is intended to encompass any arc sufficient to result in the major portion of the extraction device having a curved front face, as viewed during insertion of the device.

As used herein, the term "inflatable ring" or "insufflation ring" means a bladder capable of accepting and holding a fluid, such as air, having a vacant circular center with respect to the material forming the bladder. The ring may be a circular band, ovoid, or spherical.

As used herein, the term "interstitial space" means a hollow space, i.e. not occupied by a solid, which is bound by one or more solids in two dimensions. For example, the interstitial space may have a square cross-section, which is bound in two dimensions by four walls. Alternatively, the interstitial space may have an oval or circular cross-section, which is bound in two dimensions by a tubular structure.

As used herein, the term "laparoscopic" is meant to encompass any minimally invasive surgical technique, including endoscopy and NOTES. The term is intended to be used in its broadest sense, and not limited to specific laparoscopic techniques.

As used herein "ovoid" means having a general oval structure, such as an egg-shape in three dimensions.

As used herein, the term "patient" is directed toward humans, but can also include any member of the animal kingdom, including mammals, such as but not limited to, primates including gorillas and monkeys; rodents, such as mice, fish, reptiles and birds. The patient may be any animal requiring any surgical therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

As used herein, the term "proximal" refers to a location that, during normal use, is closer to the operator or clinician using the device and farther from the patient in connection with whom the device is used. Conversely, the term "distal" refers to a location that, during normal use, is farther from the clinician using the device and closer to the patient in connection with whom the device is used As used herein, "specimen" means at least one tissue or organ extracted during a laparoscopic procedure. Exemplary specimens include organs and tissues from the female reproductive system, such as ovarian cysts, necrotic ovary, ectopic pregnancy, uterus or uterine tissue, as well as tissues and organs from the abdomen, such as gall bladder, portions of the stomach or intestine, or appendix. As is known in the art, the examples are not an exhaustive list of organs and tissues that may be removed using the present device.

As used herein, "substantially" means largely if not wholly that which is specified but so close that the difference is insignificant.

Example

Laparoscopic instrument 1 is formed of sheath 2, having a circular or ovoid cross-section, as seen in FIG. 1(A). Sheath 2 has an interstitial space in its center, distal end 6 and proximal end 7. Sheath opening 9 is disposed distally along the length of sheath 2 and extends from the exterior space to the interstitial space of sheath 2.

Figure 2:
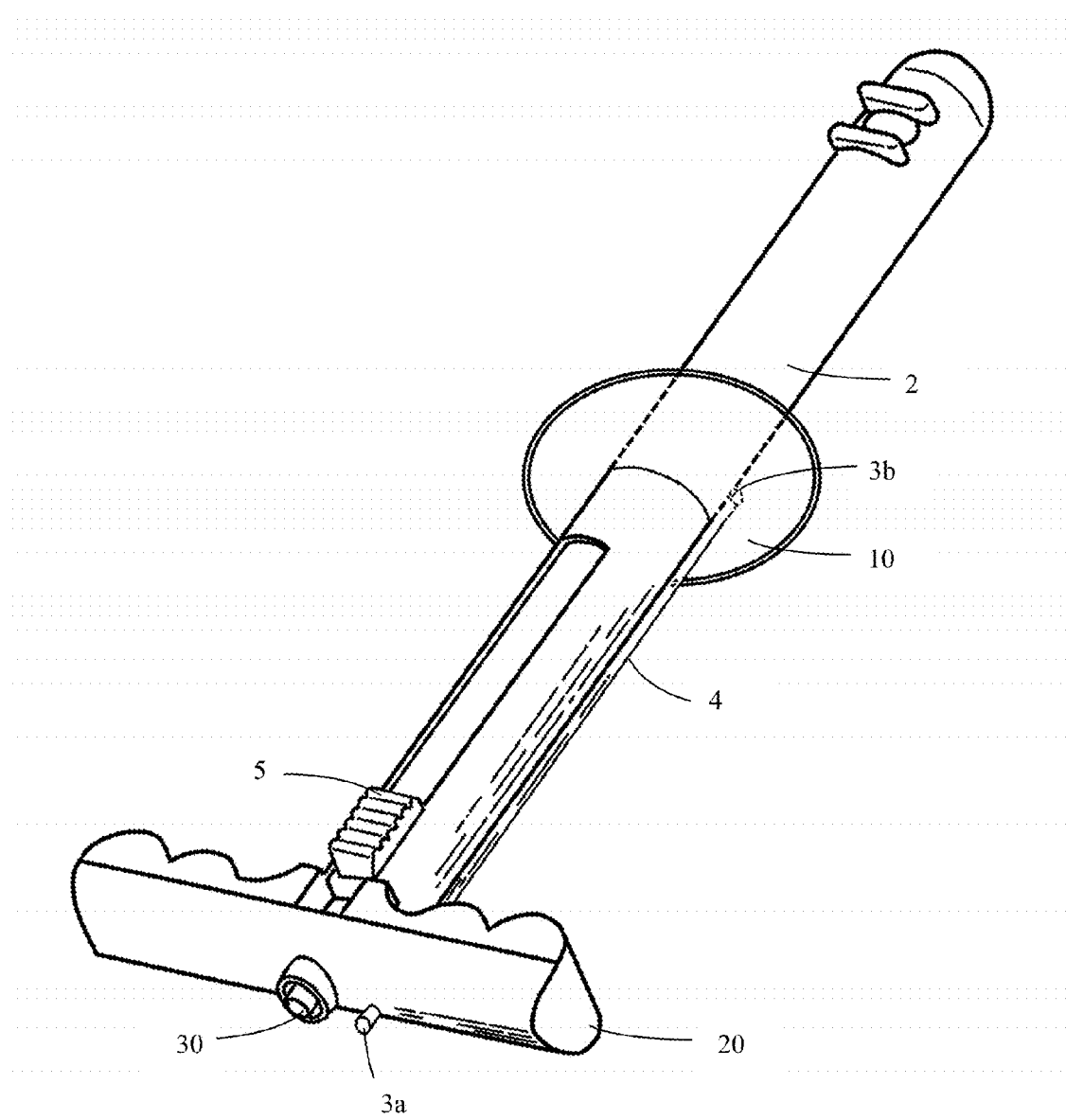
FIG. 2 is an isometric view of the laparoscopic instrument showing an external inflation channel for the occlusion balloon.
Figure 3:
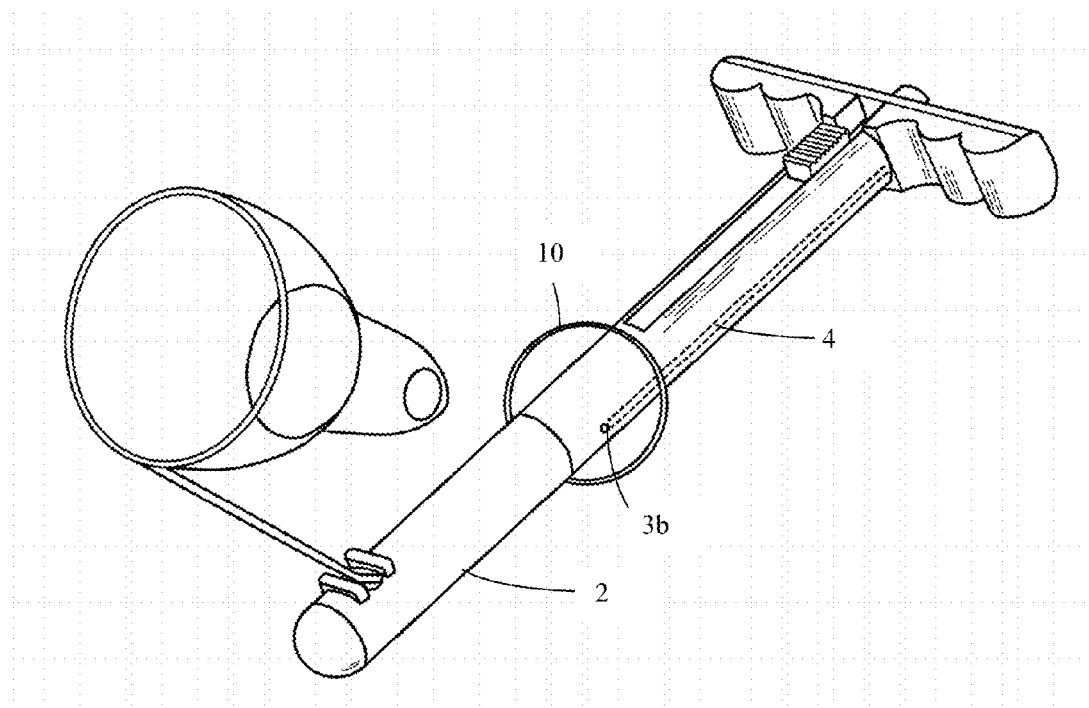
FIG. 3 is an isometric view of the laparoscopic instrument showing an internal inflation channel for the occlusion balloon.

Optional specimen bag 40, actuator mechanism 5, and handle 20, are seen in FIG. 1(B). Optional inflatable balloon 10, seen in FIG. 1(B), surrounds the sheath for providing a seal to maintain pneumoperitoneum during surgery. Inflatable balloon 10, such as a rumi balloon, and is in fluid communication with inflation channel 4. Inflation channel 4 is disposed on the outer face of sheath 2, as seen in FIG. 2. The distal end of inflation channel 4 is fused with inflatable balloon 10 or otherwise in fluid communication such that the joining of inflation channel 4 and inflatable balloon 10 does not leak fluid from the joint. The proximal end of inflation channel 4 may end in inflatable port 3a or other means to permit one of skill in the art to inflate and deflate inflatable balloon 10. Alternatively, inflation channel 4 is disposed on the interior face of sheath 2. Where inflation channel 4 is disposed on the interior wall of sheath 2, a small balloon port 3b is disposed through sheath 2, under inflatable balloon 10 and adjacent to an opening in inflatable balloon 10, as seen in FIG. 3. The distal end of inflatable channel 4 is fused to the small port, such that the distal end of inflatable channel 4, the port, and inflatable balloon 10 provide a seal. The proximal end of inflatable channel 4 may end in a port or other means to permit one of skill in the art to inflate and deflate inflatable balloon 10.

Figure 4:
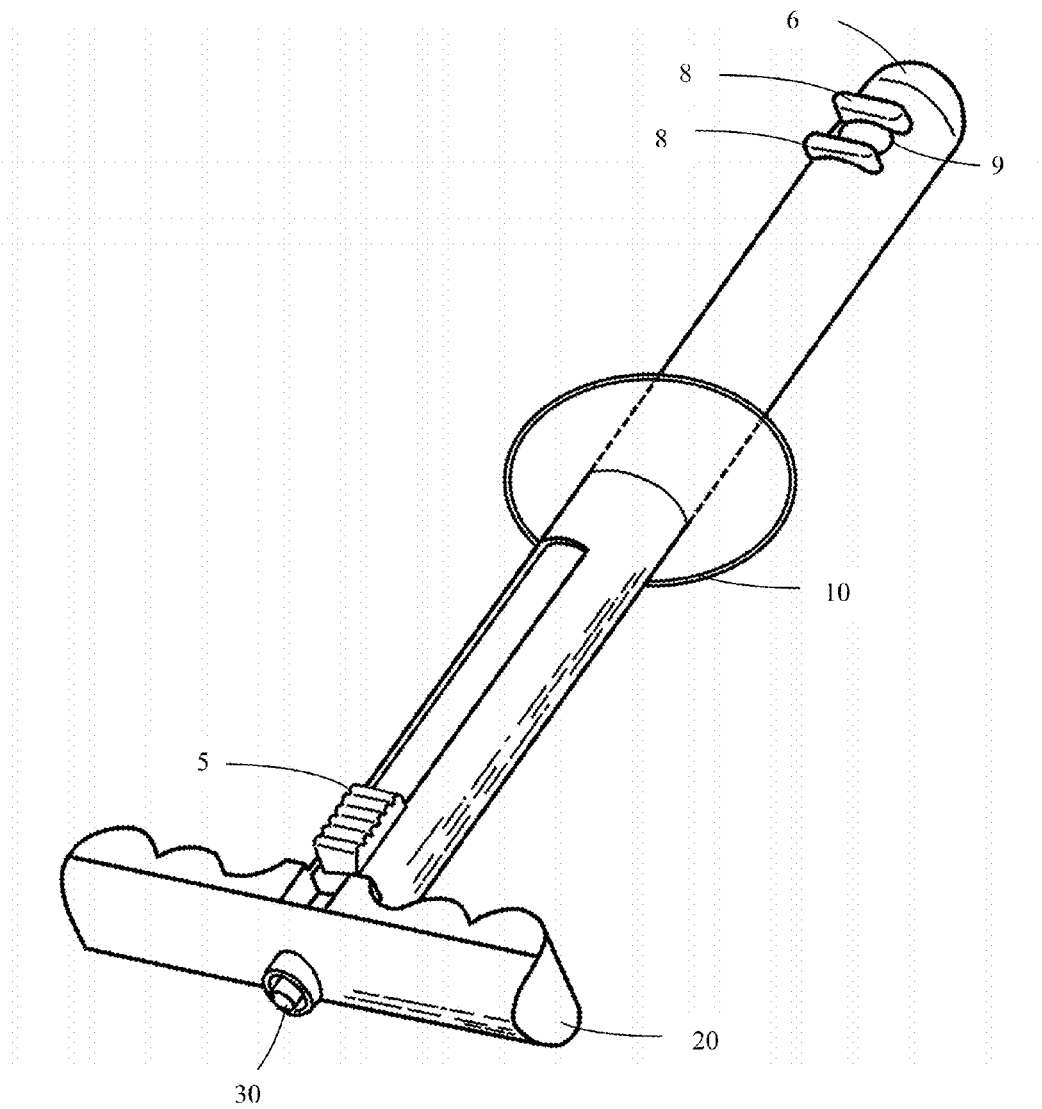
FIG. 4 is an isometric view of the present endoscopic instrument with the occlusion balloon inflated.
Figure 5:
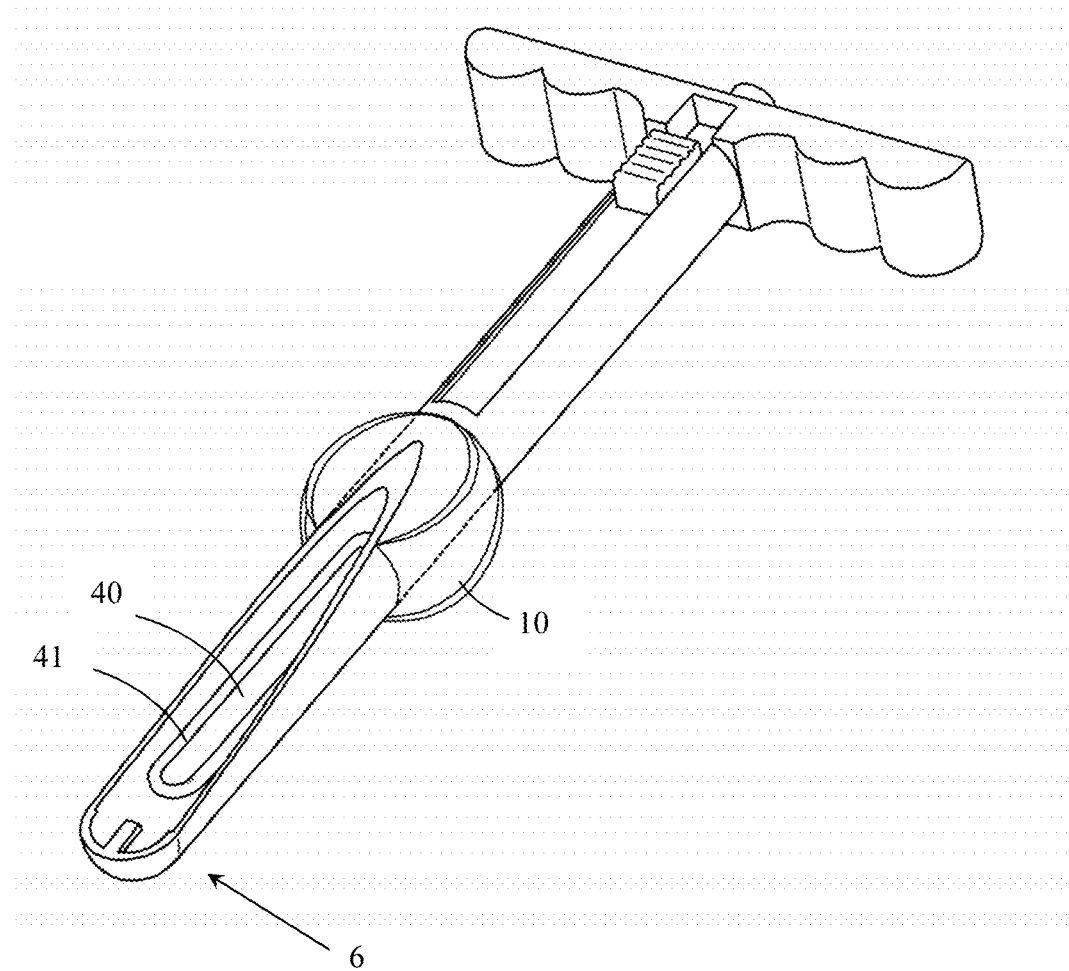
FIG. 5 is an isometric cut-away view of the present laparoscopic instrument with the occlusion balloon deflated. The internal structures of the instrument are visible through the cut-away section.

Optionally, raised features 8 are disposed on the outer face of sheath 2, one proximal to sheath opening 9, and one distal to sheath opening 9, as seen in FIG. 4. Proximal end 7 includes handle 20 for manipulating the instrument. Specimen bag 40 is disposed in the interstitial space of sheath 2, and adjacent to sheath opening 9, as seen in FIG. 5. The open end of specimen bag 40 contains deployable ring 41 that is initially compressed or folded within sheath 2, as seen in FIG. 5. Deployable ring 41 is made of any semi-flexible material known in the art, such as thin wire, thin flexible plastic, and other materials which may bend, yet forms a preformed shape upon release. Deployable ring 41 is fixed to deployment arm 42, by means known in the art, such as thermal welding, electrical welding, soldering, or a pin hinge. Deployment arm 42, which is made of any useful material known in the art, such as surgical steel, plastic, and titanium, runs the length of the sheath, and is connected to actuator mechanism 5, by means known in the art. Non-limiting examples include thermal welding, electrical welding, soldering, or a pin hinge.

Figure 6:
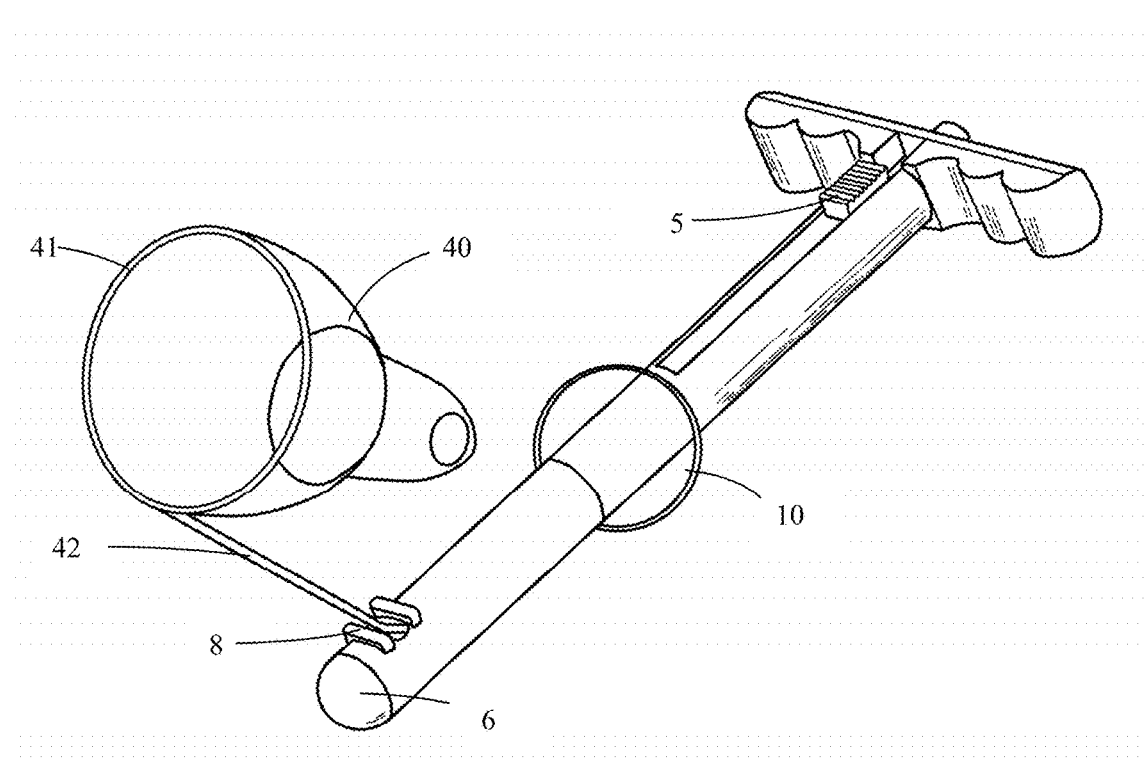
FIG. 6 is an isometric view of the laparoscopic instrument with the specimen bag being advanced through the specimen bag opening.

Actuator mechanism 5 is slidingly attached to the proximal end sheath 2, such that advancing the actuator mechanism distally extends specimen bag 40 through sheath opening 9 and permits deployable ring 41 to open into its performed shape, as seen in FIG. 6.

Figure 7:
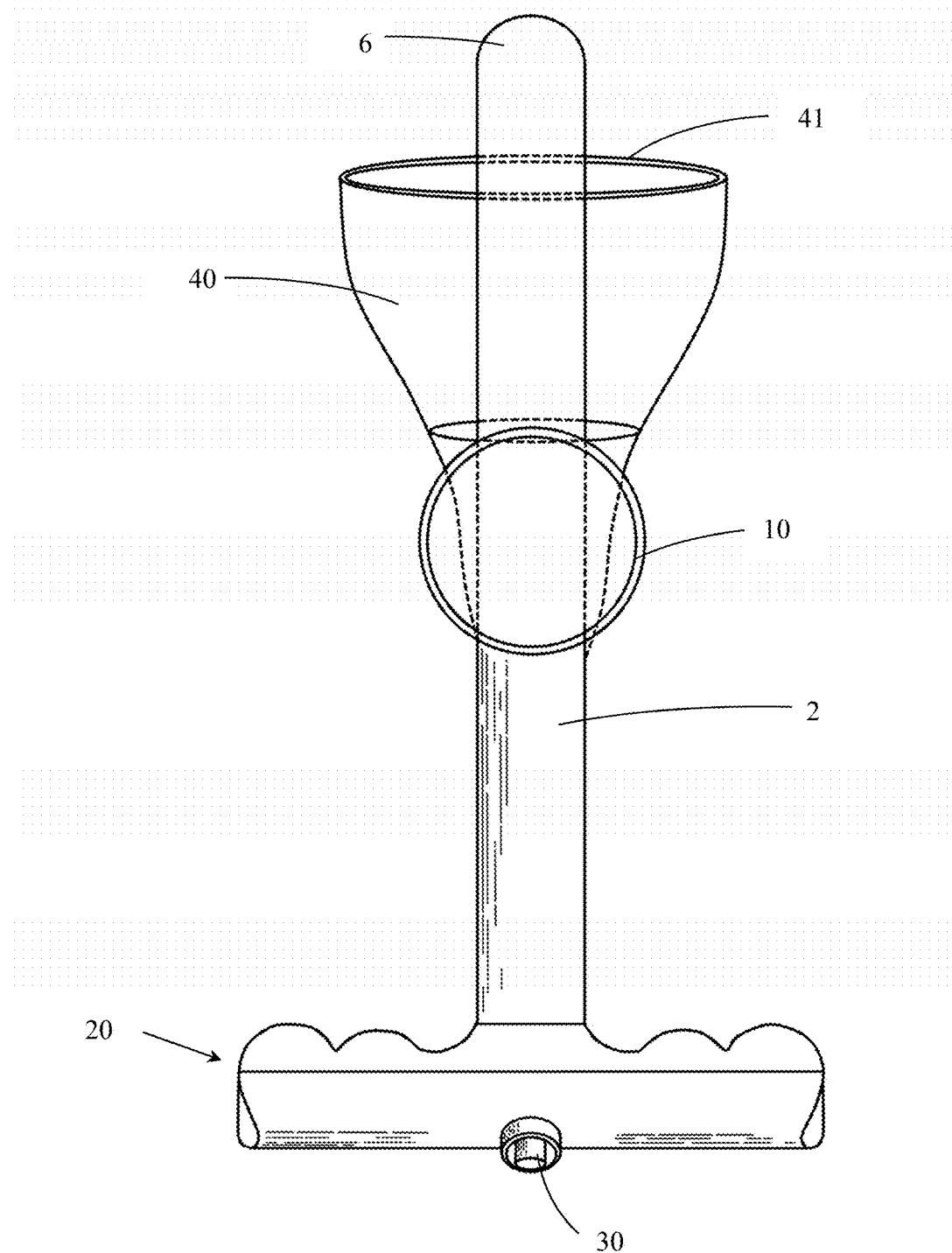
FIG. 7 is a bottom-up view of the laparoscopic instrument with the specimen bag deployed.

Optionally, laparoscopic instrument 1 provides insufflation for pneumoperitoneum during surgery. Insufflation channel 31 is disposed on the interior wall of sheath 2. While insufflation channel 31 may be disposed on any interior wall, one of skill in the art will recognize optimal position of the insufflation channel will be opposite sheath opening 9, thereby reducing the likelihood of interference with specimen bag 40. The proximal end of insufflation channel 31 is in fluid communication with insufflation port 30, which may be disposed on handle 20, as seen in FIG. 7. The distal end of insufflation channel 31 is fluid communication with distal end cap 35. A hole or other port is disposed in distal end cap 35, in communication with insufflation channel 35, thereby permitting insufflation fluids to exit insufflation channel 35 and into the patient.

Example

Laparoscopic instrument 1 comprises of sheath 2, having a circular or ovoid cross-section, a specimen bag 40, actuator mechanism 5, and handle 20, as disclosed in the previous example. However, the insufflation system of laparoscopic instrument 1 provides insufflation port 30, such as the port disposed on handle 20 seen in FIG. 7. Insufflation port 30 is in fluid communication with the interstitial space, i.e. there is no insufflation channel 31, permitting sheath opening 9 to be used to attain pneumoperitoneum.

Example

Laparoscopic instrument 1 comprises interstitial channels thereby permitting a surgeon to introduce instruments, implants, sponges, needles or other objects into the operative field during laparoscopic surgery, without having to place large ports in the abdomen or make larger incisions. Optionally, an instrument seal may be disposed on the proximal end of the sheath 2, permitting use of the laparoscopic instrument as a laparoscopic port. The instrument seal is constructed of a compound capable of forming an air-tight seal, such as polyester, para-phenylenediamine and terephthaloyl chloride polymer, carbon fiber, expanded PTFE, meta-phenylenediamine and terephthaloyl chloride polymer, nylon, fiber glass, cotton, polypropylene and ceramic, rubber, latex, silicone, polyurethane, polyisoprene, polystyrene and polybutadiene polymer, urethane, polyethylene, polyisoprene, polyvinylchloride, ethylene propylene diene monomer, neoprene, and styrene butadiene. In specific embodiments, instrument seal is also coated in at least one additional compound. Useful compounds are hydrophilic polymer coatings, Teflon, thermoplastic, cyanoacrylate, parylene, plasma surface treatments, cornstarch powder, silicone oil, silicone grease, astroglide lubricants, mineral oil, glycerin, alcohol, saline, Teflon lubricants, Krytox lubricants, molybdenum disulfide lubricants, and graphite.

Example

The laparoscopic instrument may safely facilitate entry into the abdominal cavity during laparoscopic surgery. Traditionally, peritoneal access has been obtained by a trans-abdominal approach. The Veress needle, which was originally developed to perform pleurodesis in tuberculosis patients, is commonly used to access the abdominal cavity and provide pneumoperitoneum. One disadvantage is the blind placement of the needle into the abdomen and the risk of injury to adjacent organs and blood vessels.

One method, reported in 1971 by Harry Hasson and now called the open technique, has overcome this blind entry to access the peritoneal cavity (Hasson, H. M. A modified instrument and method for laparoscopy. Am J Obstet Gynecol 110: 886-887; 1971). Also, some advances in optical trocar design have allowed for visualizing entry with the use of the laparoscope that often, but not necessarily, requires prior pneumoperitoneum. However, these techniques continue to use trans-abdominal entry, most commonly through the umbilicus, with the attributed risk for vital organ and vascular injury using this approach.

The laparoscopic instrument can allow for direct entry into the posterior cul-de-sac, or Pouch of Douglas, through the posterior portion of the vagina, which is perhaps the safest access site into the abdominal cavity. As the vagina is elastic, the posterior apex of the vagina is displaced away from the rectosigmoid, and provides a safe entry even in difficult surgical procedures. Combined with the relative ease of repair of the incision, colpotomy access to the abdominal cavity is safe for patients and convenient for surgeons.

Figure 8:
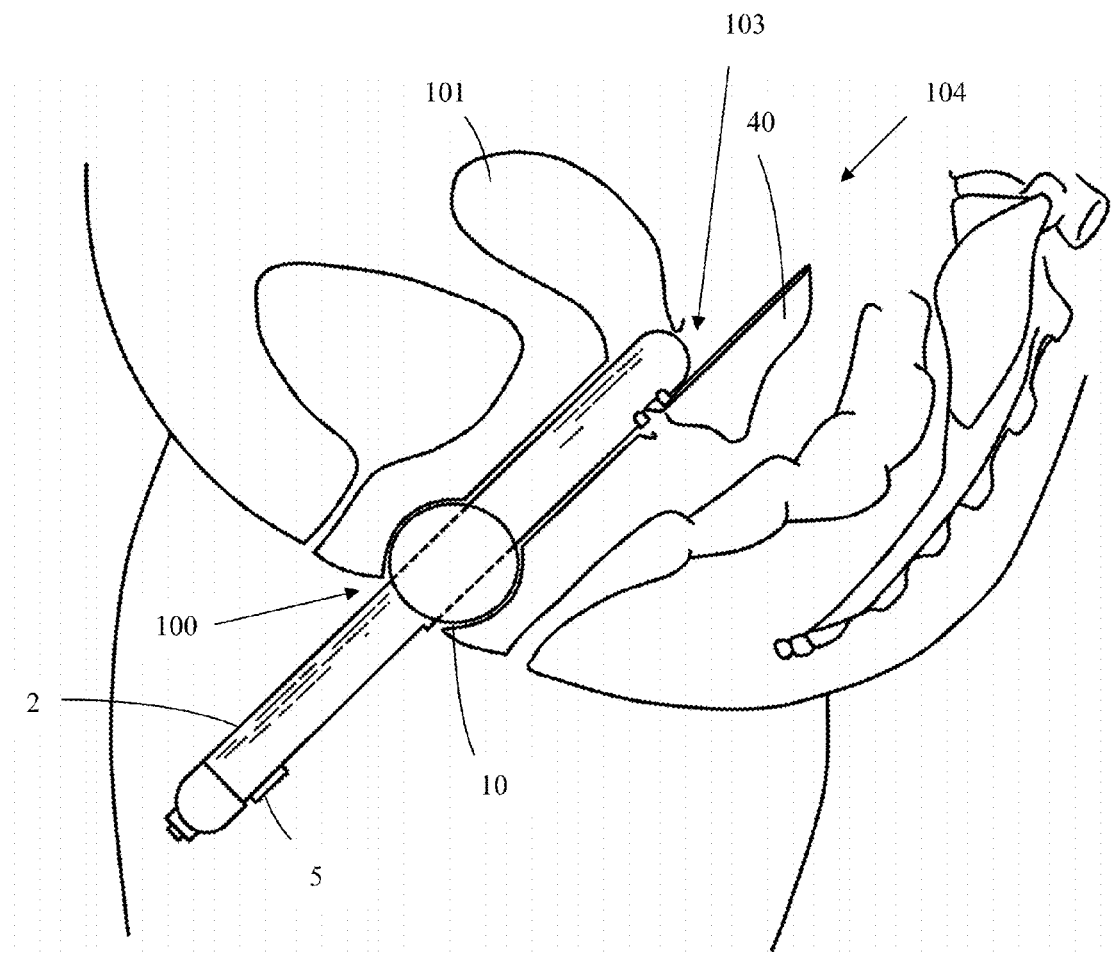
FIG. 8 is a side elevation view of the laparoscopic instrument inserted into a cut-away illustration of a vagina.

Laparoscopic instrument 1 is introduced into vagina 100, distal end first, to the upper portion of a patient's vagina and posterior to the cervix in a patient with a uterus/cervix 101 intact, as seen in FIG. 8. Inflatable balloon 10 is oriented to approximately at the opening of the vagina. An air pump or other air source, such as $CO_2$ gas, is connected to inflatable channel 4, and air flowed through inflatable channel 4 to inflate inflatable balloon 10, thereby occluding the outlet of the vagina to prevent loss of pneumoperitoneum during surgery.

The raised features 8 provide a visual and haptic target for placement of an incision in the posterior cul-de-sac (i.e. pouch of Douglas) 103 by the surgical instruments inserted into abdominal cavity 104 during traditional laparoscopic surgery. Raised features 8 enable the laparoscopic surgeon to make a transverse incision between these elevated surfaces at the apex of the vagina. This type of incision in the posterior vaginal wall is called a posterior colpotomy, and is technically challenging for most surgeons to perform without a visible or tactile guide. The incision is made from above, or within the abdominal cavity, using laparoscopic instruments, and accordingly requires that pneumoperitoneum has already been obtained.

An incision was made in the pouch of Douglas and distal end 6 of laparoscopic instrument 1 was placed into the incision. Alternatively, a posterior colpotomy incision can be made, through which the distal end of the sheath may be introduced directly. Upon creation of the vaginal incision, the surgeon positioned distal end cap 35 such that insufflation channel 31 was directed toward the abdominal cavity.

An air source, or $CO_2$ gas, was attached to insufflation port 30 and pneumoperitoneum established.

Figure 9:
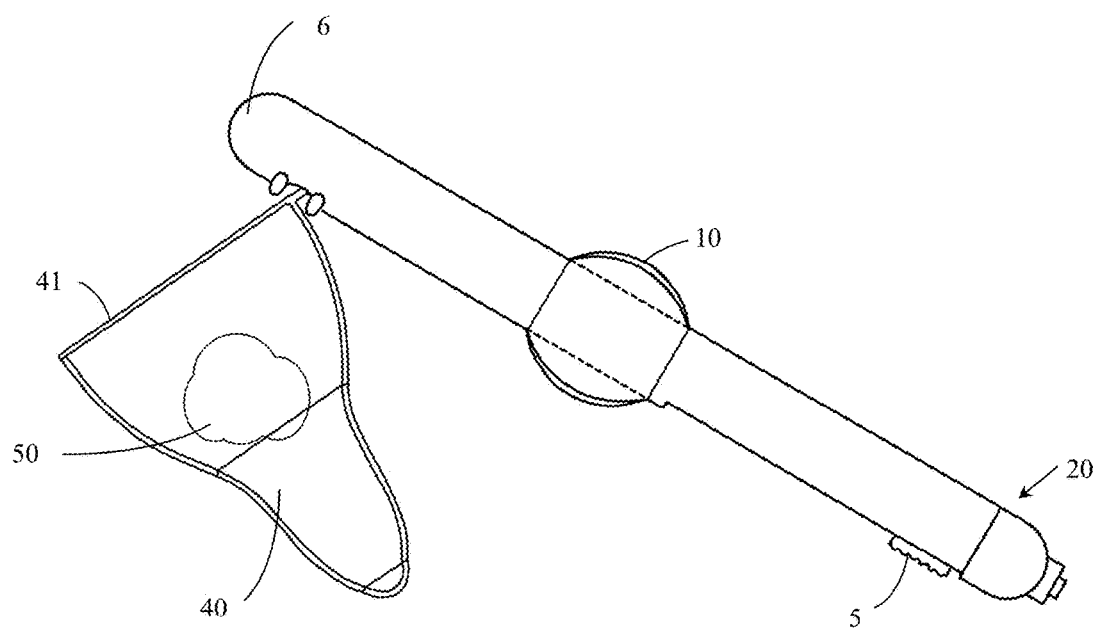
FIG. 9 is an isometric view of the laparoscopic instrument with the specimen bag being deployed.

Sheath opening 9 was aligned with the vaginal incision and actuator mechanism 5 advanced distally, causing deployment arm 42 to advance distally and extending specimen bag 40 through sheath opening 9, through the vaginal incision and into the patient's abdominal cavity. Upon insertion into the patient's abdomen, deployable ring 11 rebounded to its preformed shape, opening specimen bag 40, as seen in FIGS. 7 and 9. When deployable ring 11 is clear of sheath opening 9 and the vagina incision, the deployable ring springs open to a diameter that is sufficiently large to accommodate a specimen 50. The deployable ring and open end of the specimen bag are held in place by the actuator mechanism.

Specimen 50 is placed into specimen bag 40 with laparoscopic tools, as seen in FIG. 9. After placement of specimen 50 into specimen bag 40, the surgeon pulls on actuator mechanism 5, causing the deployable ring 41 to retract into sheath 2, thereby causing the deployable ring to return into the sheath and closing the specimen bag 40. Inflatable balloon 10 was then deflated, and actuator mechanism 5 retracted, withdrawing specimen bag 40 at least partially into sheath 2. Sheath 2 was thereafter removed from the vagina, removing the specimen. Depending on size, specimen 50 may be removed by enlarging the incision in the vagina, or may be morcellated within the specimen bag in the abdominal cavity to facilitate removal of the specimen bag through the incision in the vagina.

Example

Figure 10:
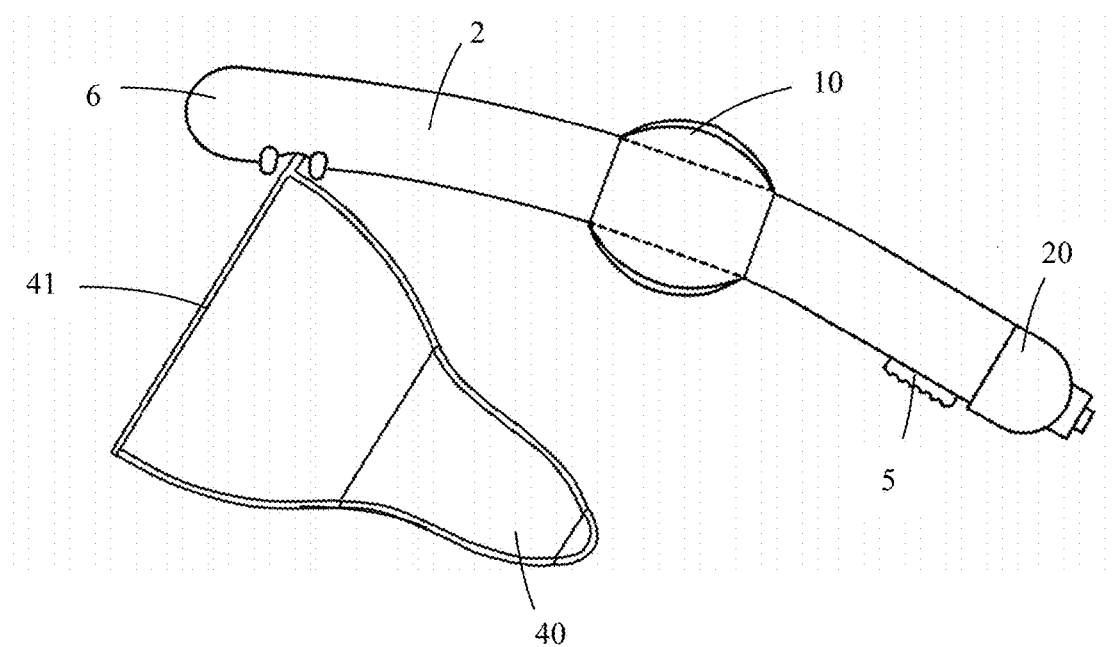
FIG. 10 is a side elevation view of the laparoscopic instrument depicted in an alternative embodiment having a curved shaft.

Laparoscopic instrument 1 optionally comprises a curved sheath 2, having a specific radius to assist in the placement of device, as seen in FIG. 10. The curve of the sheath permits the vagina to be moved out of the way of the surgeon during surgical procedures. The laparoscopic instrument is introduced into the vagina at an angle, distal end first, to the upper portion of a patient's vagina and posterior to the cervix in a patient with a uterus/cervix intact. Inflatable balloon 10 is oriented as described above and inflated using an air source, such as $CO_2$ gas, to occlude the outlet of the vagina as in the previous examples.

Optional raised features 8 are provided as described in the previous examples and an incision made in the pouch of Douglas and distal end 6 of laparoscopic instrument 1 was placed into the incision. The surgeon positions distal end cap 35 toward the abdominal cavity and pneumoperitoneum established using an air source, like $CO_2$ gas, as described in previous examples. Specimen bag 40 is utilized to collect specimen 50 as described in the previous examples. During the surgical procedure, where the surgeon requires translation of the vagina, for example to retract the vagina from the surgical field, the surgeon may articulate the handle, thereby rotating the curved sheath and the vagina.

Example

Access to the pouch of Douglas can be made by simply cutting through the vagina, posterior to the cervix, without requiring pneumoperitoneum. After the surgeon introduces the sheath through the colpotomy, inflatable balloon 10 is inflated, and actuator mechanism 5 advanced distally, deploying specimen bag 40 into the patient's abdominal cavity. The surgeon has the option of insufflating the patient using insufflation channel 31 and insufflation port 30, located at the proximal end of laparoscopic instrument 1, or maintain pneumoperitoneum following sheath placement.

After placement of the specimen into the collection bag, the surgeon retracts the specimen bag using actuator mechanism 5, causing deployable ring 41 to retract into the sheath, thereby closing the specimen bag. The inflatable balloon 10 is deflated, and the sheath is removed from the vagina, leaving the closed specimen bag in place. The bag may be attached to a string to facilitate removal. For example, a string attached to the bag opening using a noose or other sliding knot, allowing the surgeon to close the bag and remove the bag concurrently. The bag may be removed by enlarging the incision in the vagina, or by morcellating the specimen within the bag in the abdominal cavity to facilitate removal through the existing incision in the vagina. The colpotomy incision may then be closed laparoscopically or through the vagina using standard suturing techniques.

Example

Laparoscopic instrument 1 is used to remove a structure from the female reproductive system, such as a hysterectomy. The laparoscopic instrument is introduced into the vagina and inflatable balloon 10 is oriented as described above and inflated using an air source, such as $CO_2$ gas, to occlude the outlet of the vagina as in the previous examples. Specimen bag 40 is utilized is utilized to collect specimen 50 as described in the previous examples.

Example

Figure 11:
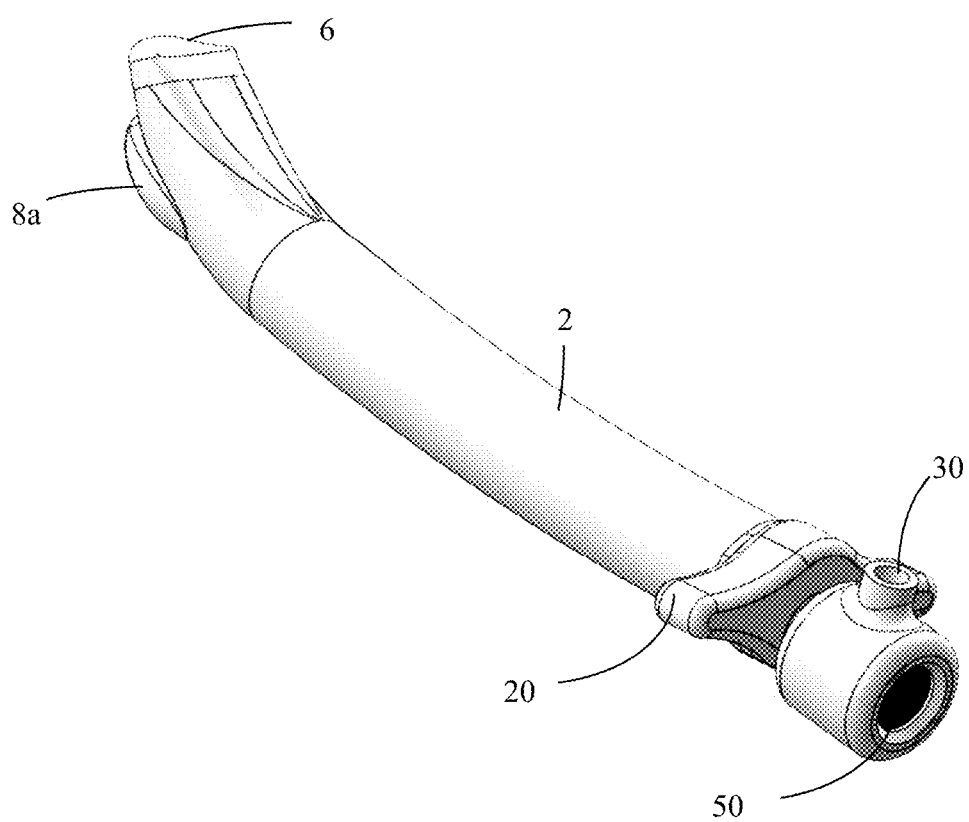
FIG. 11 is an isometric view of an instrument channel variant of the laparoscopic instrument having a curved shaft.
Figure 12:
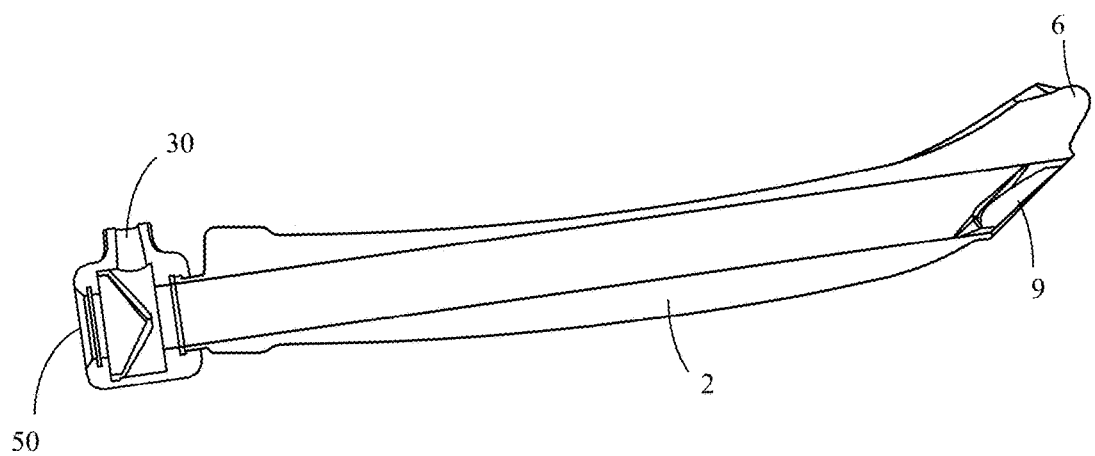
FIG. 12 is a cross-section view of an instrument channel variant of the laparoscopic instrument having a curved shaft and straight instrument channel.
Figure 13:
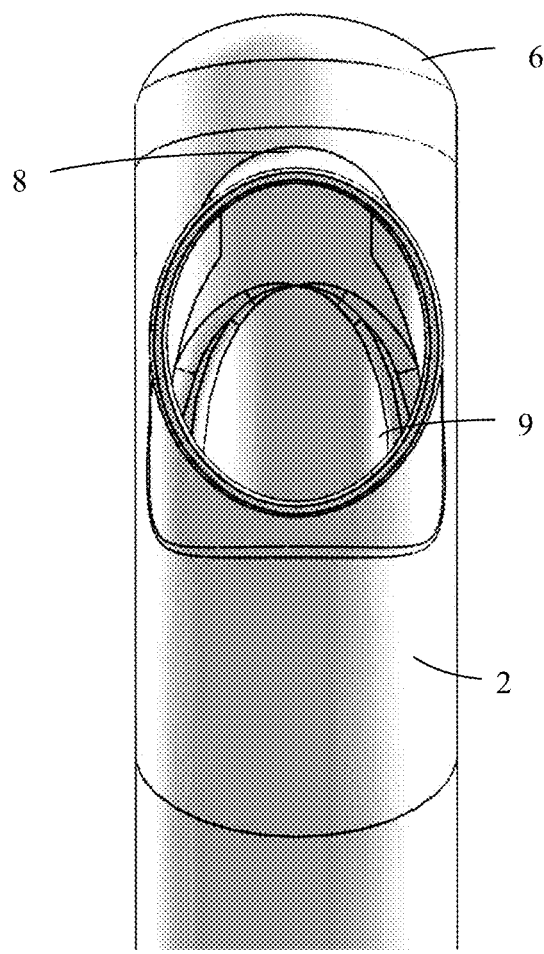
FIG. 13 is a top-down view of an instrument channel variant of the laparoscopic instrument having a curved shaft showing the instrument channel opening.

Laparoscopic instrument 1 optionally comprises a curved sheath 2, comprising interstitial space 60, seen in FIG. 11. Instrument channel 65 is disposed in curved sheath 2, and is adapted to accept laparoscopic surgical tools, such as instruments, implants, sponges, needles or other objects. The instrument channel is fixed within interstitial space 60 on the proximal and distal ends of the instrument channel to the interior walls of curved sheath 2 by means known in the art, such as thermal welding. Alternatively, instrument channel 65 is formed in a solid curved sheath 2, i.e. the instrument channel forms interstitial space 60, as seen in FIG. 12. Instrument seal 50 is disposed on the proximal end of instrument channel 65 and forms a seal against any laparoscopic tools used, thereby maintaining pneumoperiotoneum. Instrument channel 65 may have a curve or be straight, fitting in sheath 2 as seen in FIG. 12, and may end in the distal end of sheath 2 or on the wall of the sheath 2, as seen in FIG. 13. Insufflation port 30 is disposed on instrument seal 50, distally to the seal itself, thereby providing a means for the surgeon to establish pneumoperiotoneum, Optionally, insufflation port 30 is in fluid communication with the proximal end of insufflation channel 31, which runs the length of the laparoscopic instrument or a portion thereof.

Figure 14:
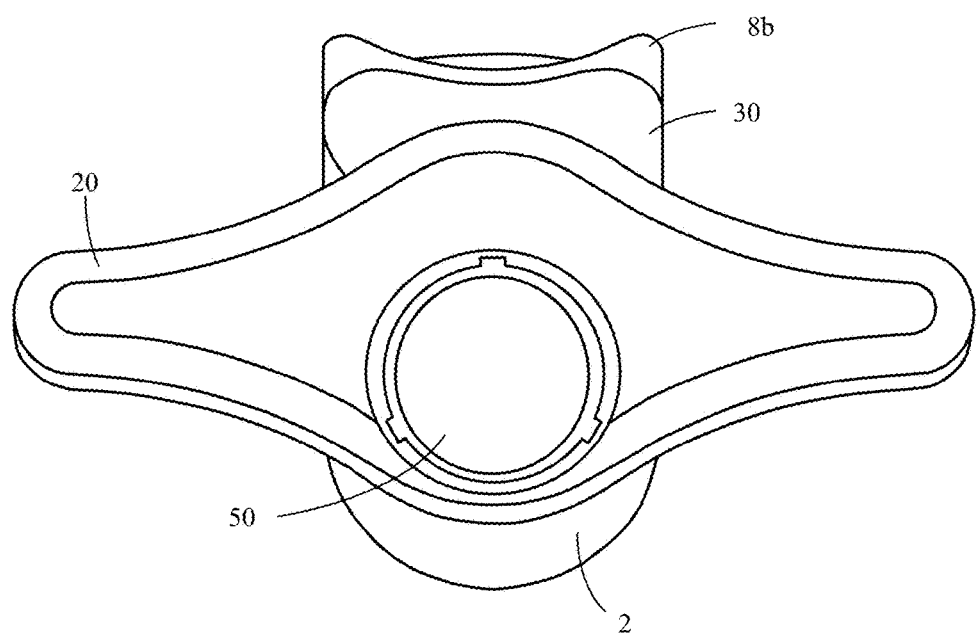
FIG. 14 is side view of the proximal end of an instrument channel variant of the laparoscopic instrument.
Figure 15:
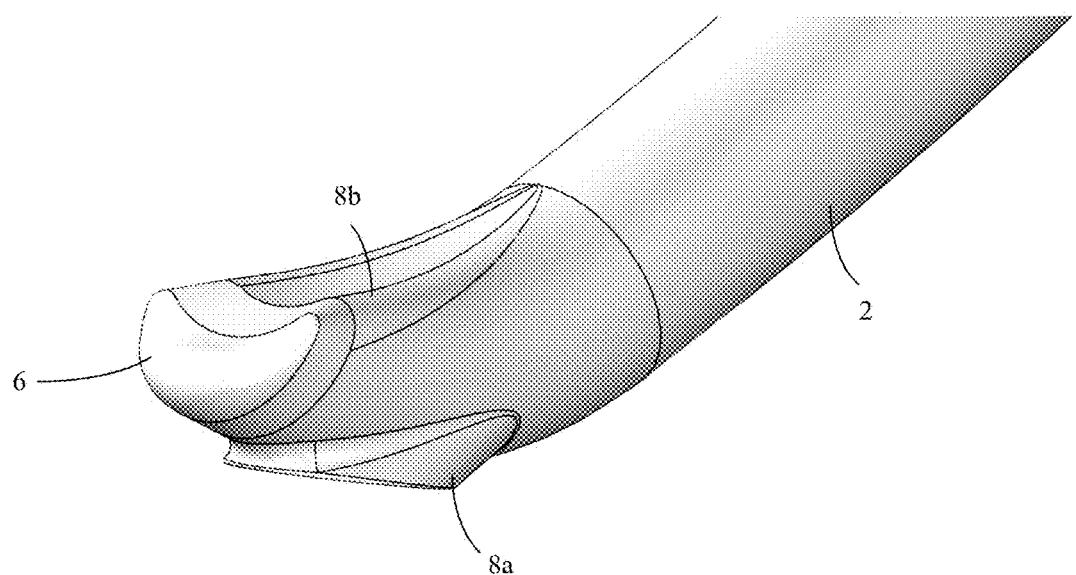
FIG. 15 is an isometric view of the distal end of an instrument channel variant of the laparoscopic instrument having a curved shaft.

Distal end 6 of sheath 2 ends in a rounded tip, seen in FIG. 12, facilitating insertion of the laparoscopic instrument with minimal risk of injury. Lower raised features 8a and upper raised features 8b, seen in FIGS. 14 and 15, are used to orient the laparoscopic instrument. The raised features provide a visual and/or haptic guide during surgery, though may also provide a lip function to protect the patient from injury during introduction of instruments that may have blades or other sharp components. Optionally, the at least upper and lower feature, are alternatively a lip which completely encircles the opening.

The laparoscopic instrument may be used intravaginally, as described above, or inserted into the abdomen through an opening, as in abdominal laparoscopic surgeries. The upper and lower raised features, 8a and 8b, are used to orient the instrument adjacent to the abdominal side of the vaginal wall and an incision made, permitting access to the vagina. Sheath opening 9 was moved adjacent to the opening in the vaginal wall and instruments inserted into the vagina and surgery performed. Where a tissue is removed, it may be placed into a specimen bag and removed through laparoscopic instrument 1 or through the vagina using a string.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of an transvaginal specimen extractor, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A laparoscopic instrument, comprising:
    a tubular shaft having a proximal end and a distal end;
    at least one interstitial space disposed in the tubular shaft;
    an opening disposed on a wall of the tubular shaft on the distal end of the shaft, extending from the at least one interstitial space to an exterior of the tubular shaft;
    a plurality of raised features disposed on an exterior of the wall of the tubular shaft, wherein each of the plurality of raised features has a common endpoint or border with the opening;
    wherein the plurality of raised features comprises a first raised feature disposed proximal to the opening and a second raised feature disposed distal to the opening, where the first raised feature and the second raised feature are not directed directly connected to one another; and
    an insufflation port disposed on the proximal end of the tubular shaft.

2. The laparoscopic instrument of claim 1, further comprising a closed hemispherical end disposed on the distal end of the shaft.

3. The laparoscopic instrument of claim 1, wherein the tubular shaft is made of plastic, resin, or metal.

4. The laparoscopic instrument of claim 1, further comprising a handle disposed on the proximal end of the shaft.

5. The laparoscopic instrument of claim 1, wherein the insufflation port is disposed on a handle, wherein the handle is disposed on the proximal end of the tubular shaft.

6. The laparoscopic instrument of claim 1, further comprising an insufflation channel disposed in the at least one interstitial space of the tubular shaft having a proximal end and a distal end, wherein the insufflation channel is in fluid communication with the insufflation port on the proximal end of the tubular shaft.

7. The laparoscopic instrument of claim 6, wherein the distal end of the insufflation channel is disposed on the distal end of the tubular shaft.

8. The laparoscopic instrument of claim 1, wherein the tubular shaft is curved.

9. The laparoscopic instrument of claim 1, further comprising an inflatable balloon disposed on an exterior face of the tubular shaft and wherein the inflatable balloon is in fluid communication with an inflation source.

10. The laparoscopic instrument of claim 9, wherein the inflatable balloon is in fluid communication with a distal end of an inflation channel, where the inflation channel is disposed on the exterior face of the tubular shaft or disposed on an interior face of the tubular shaft.

11. The laparoscopic instrument of claim 10, wherein a proximal end of the inflation channel is in fluid communication with an inflation port.

12. The laparoscopic instrument of claim 1, further comprising at least one surgical instrument channel disposed in the at least one interstitial space of the tubular shaft, wherein the at least one instrument channel runs a length of the tubular shaft and has a proximal end and a distal end; and at least one instrument seal disposed on the proximal end of the at least one instrument channel.

13. A method of performing laparoscopic removal of a specimen from a patient, comprising the steps:
    providing a laparoscopic instrument, wherein the laparoscopic instrument comprises:
        a tubular shaft having a proximal end and a distal end;
        at least one interstitial space disposed in the tubular shaft;
        a specimen bag opening disposed on a wall of the tubular shaft on the distal end of the shaft, extending from the at least one interstitial space to an exterior of the tubular shaft;
        a plurality of raised features disposed on an exterior of the wall of the tubular shaft, wherein each of the plurality of raised features has a common endpoint or border with the specimen bag opening
        wherein the plurality of raised features comprises a first raised feature disposed proximal to the specimen bag opening and a second raised feature disposed distal to the specimen bag opening, where the first raised feature and the second raised feature are not directly connected to one another;
        an insufflation port disposed on the proximal end of the tubular shaft;
        a deployable specimen collector disposed within the tubular shaft, further comprising:
            a specimen bag having an open end and a closed end;
            a deployable ring disposed on the open end of the specimen bag;
            a specimen bag support in communication with the deployable ring,
            wherein the specimen bag support is connected to an actuator mechanism;
            wherein the deployable ring is disposed adjacent to the specimen bag opening;
            the actuator mechanism disposed along a length of the shaft or a portion thereof;
    introducing the laparoscopic instrument into a patient's vagina;
    positioning the laparoscopic instrument adjacent to a structure in the patient's vagina;
    extending the specimen bag through the specimen bag opening;
    placing the specimen in the specimen bag;

retracting the specimen bag; and withdrawing the laparoscopic instrument from the patient's vagina.

14. The method of claim 13, further comprising insufflating the patient comprising the steps:

providing an insufflation system in the laparoscopic instrument, wherein the insufflation system comprises:

a closed insufflation system, further comprising:

the insufflation port disposed on a proximal half of the laparoscopic instrument;

an insufflation channel having a proximal end and a distal end, wherein the proximal end of the insufflation channel is in fluid communication with the insufflation port;

a port disposed on a distal end of the laparoscopic instrument, wherein the distal end of the insufflation channel is in fluid communication with the port;

or an open insufflation system, further comprising:

the insufflation port disposed on the proximal half of the laparoscopic instrument, wherein a distal end of the insufflation port is in fluid communication with the at least one interstitial space of the tubular shaft;

introducing a fluid into the insufflation system, wherein the fluid insufflates the patient.

15. The method of claim 14, wherein the fluid is air or $CO_2$ gas.

16. The method of claim 13, further comprising sealing a vaginal opening to maintain insufflation, comprising the steps:

providing an inflatable balloon on the laparoscopic instrument, wherein the inflatable balloon is disposed on an exterior face of the tubular shaft and wherein the inflatable balloon is in fluid communication with an inflation source; and introducing a fluid into the inflatable balloon, wherein the fluid inflates the inflatable balloon.

17. The method of claim 16, wherein the fluid is air or $CO_2$ gas.

* * * * *